United States Patent
Kudlik

(10) Patent No.: US 12,133,977 B2
(45) Date of Patent: *Nov. 5, 2024

(54) COST FUNCTION FOR RESPONSE ALGORITHM

(71) Applicant: Medtronic, Inc., Minneapolis, MN (US)

(72) Inventor: D'Anne E. Kudlik, Saint Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/057,085

(22) Filed: Nov. 18, 2022

(65) Prior Publication Data
US 2023/0077463 A1    Mar. 16, 2023

Related U.S. Application Data

(63) Continuation of application No. 16/796,017, filed on Feb. 20, 2020, now Pat. No. 11,504,520.

(51) Int. Cl.
*A61M 60/50* (2021.01)
*A61M 60/205* (2021.01)
*G16H 40/63* (2018.01)

(52) U.S. Cl.
CPC .......... *A61M 60/50* (2021.01); *A61M 60/205* (2021.01); *G16H 40/63* (2018.01)

(58) Field of Classification Search
CPC ...... A61M 60/50; A61M 60/205; G16H 40/63
See application file for complete search history.

(56) References Cited

U.S. PATENT DOCUMENTS

| | | | |
|---|---|---|---|
| 7,997,854 B2 | 8/2011 | LaRose et al. | |
| 8,007,254 B2 | 8/2011 | LaRose et al. | |
| 8,419,609 B2 | 4/2013 | Shambaugh, Jr. et al. | |
| 8,506,471 B2 | 8/2013 | Bourque | |
| 8,512,013 B2 | 8/2013 | LaRose et al. | |
| 8,961,388 B2 | 2/2015 | Bourque | |
| 9,492,601 B2 * | 11/2016 | Casas | A61M 60/546 |
| 9,561,313 B2 | 2/2017 | Taskin | |
| 9,801,988 B2 | 10/2017 | Bourque | |
| 10,077,777 B2 | 9/2018 | Horvath et al. | |
| 11,235,139 B2 * | 2/2022 | Kudlik | A61M 60/178 |

(Continued)

FOREIGN PATENT DOCUMENTS

WO    2014197558 A2    12/2014

OTHER PUBLICATIONS

International Search Report and Written Opinion dated Apr. 9, 2021, for corresponding International Application No. PCT/US2021/016000; International Filing Date: Feb. 1, 2021 consisting of 10-pages.

(Continued)

*Primary Examiner* — Shirley X Jian
(74) *Attorney, Agent, or Firm* — Shumaker & Sieffert, P.A.

(57) ABSTRACT

A controller for an implantable blood pump includes processing circuitry configured to initiate a suction response algorithm if a combination of a number of detected suction events multiplied by a suction event variable and a number of non-suction events multiplied by a non-suction event variable exceed a predetermined threshold.

17 Claims, 2 Drawing Sheets

(56) References Cited

U.S. PATENT DOCUMENTS

| | | | | |
|---|---|---|---|---|
| 11,504,520 B2* | 11/2022 | Kudlik | ............... | A61M 60/178 |
| 11,617,877 B2* | 4/2023 | Kemmerer | .......... | A61M 60/178 |
| | | | | 600/17 |
| 11,617,878 B2* | 4/2023 | Kudlik | ............... | A61M 60/538 |
| | | | | 600/16 |
| 11,666,281 B2* | 6/2023 | Kudlik | ............... | A61M 60/523 |
| | | | | 600/526 |
| 11,694,539 B2* | 7/2023 | Kudlik | ................... | G08B 21/24 |
| | | | | 340/539.11 |
| 2014/0323796 A1 | 10/2014 | Medvedev et al. | | |
| 2016/0058929 A1 | 3/2016 | Medvedev et al. | | |
| 2016/0058930 A1 | 3/2016 | Medvedev et al. | | |
| 2018/0028738 A1 | 2/2018 | Brown et al. | | |
| 2019/0351116 A1* | 11/2019 | Kudlik | ............... | A61M 60/546 |
| 2020/0275890 A1* | 9/2020 | Kudlik | ............... | A61M 60/422 |
| 2021/0260263 A1 | 8/2021 | Kudlik et al. | | |
| 2021/0260264 A1 | 8/2021 | Kudlik | | |

OTHER PUBLICATIONS

Prosecution History from U.S. Appl. No. 16/796,017, dated Mar. 23, 2022 through Jul. 25, 2022, 34 pp.

* cited by examiner

COST FUNCTION FOR RESPONSE ALGORITHM

This application is a continuation of U.S. patent application Ser. No. 16/796,017, filed Feb. 20, 2020, the entire content of which is incorporated herein by reference.

FIELD

The present technology is generally related to implantable blood pumps and a function for initiating a suction response algorithm.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as a ventricular assist device or "VAD." Where a VAD is used to assist the pumping action of the left ventricle, the device draws blood from the left ventricle of the heart and discharges the blood into the aorta.

If a VAD is operated at a flow rate in excess of an inflow rate of blood to the ventricle, the VAD will create a suction condition within the ventricle, wherein the ventricle is collapsed and essentially devoid of blood. This condition is undesirable. In this condition, the flow rate through the pump will decline rapidly. Likewise, if the intake or outlet of the pump is occluded, the flow rate will decline. If the flow rate through the pump is insufficient, the device will not provide sufficient circulatory assistance to the patient. Excessive flow also can create undesirable conditions.

SUMMARY

The techniques of this disclosure generally relate to implantable blood pumps and a function for initiating a suction response algorithm.

In one aspect a controller for an implantable blood pump includes processing circuitry configured to initiate a suction response algorithm if a combination of a number of detected suction events multiplied by a suction event variable and a number of non-suction events multiplied by a non-suction event variable exceed a predetermined threshold.

In another aspect of this embodiment, the predetermined threshold is at least one.

In another aspect of this embodiment, the suction event variable is less than one.

In another aspect of this embodiment, the suction event variable is 0.2.

In another aspect of this embodiment, the non-suction event variable is less than one.

In another aspect of this embodiment, the non-suction event variable is 0.05.

In another aspect of this embodiment, each detected suction event and non-suction event is determined over a one-second time period.

In another aspect of this embodiment, the suction response algorithm is initiated if the combination of a number of detected suction events multiplied by a suction event variable and a number of non-suction events multiplied by a non-suction event variable exceed a predetermined threshold during a predetermined time interval.

In another aspect of this embodiment, the predetermined time interval is 30 seconds.

In another aspect of this embodiment, the combination of a number of detected suction events multiplied by a suction event variable and a number of non-suction events multiplied by a non-suction event variable is at least zero.

In one aspect, a method of operating an implantable blood pump includes initiating a suction response algorithm if a combination of a number of detected suction events multiplied by a suction event variable and a number of non-suction events multiplied by a non-suction event variable exceed a predetermined threshold.

In another aspect of this embodiment, the predetermined threshold is at least one.

In another aspect of this embodiment, the suction event variable is less than one.

In another aspect of this embodiment, the suction event variable is 0.2.

In another aspect of this embodiment, the non-suction event variable is less than one.

In another aspect of this embodiment, the non-suction event variable is 0.05.

In another aspect of this embodiment, each detected suction event and non-suction event is determined over a one-second time period.

In another aspect of this embodiment, the suction response algorithm is initiated if the combination of a number of detected suction events multiplied by a suction event variable and a number of non-suction events multiplied by a non-suction event variable exceed a predetermined threshold during a predetermined time interval.

In another aspect of this embodiment, the predetermined time interval is 30 seconds.

In one aspect, a controller for an implantable blood pump includes processing circuitry configured to initiate a suction response algorithm if a combination of a number of detected suction events multiplied by a suction event variable less than one and a number of non-suction events multiplied by a non-suction event variable less than one and less than the suction event variable exceed a predetermined threshold, each detected suction event and non-suction event being determined over a one-second interval.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
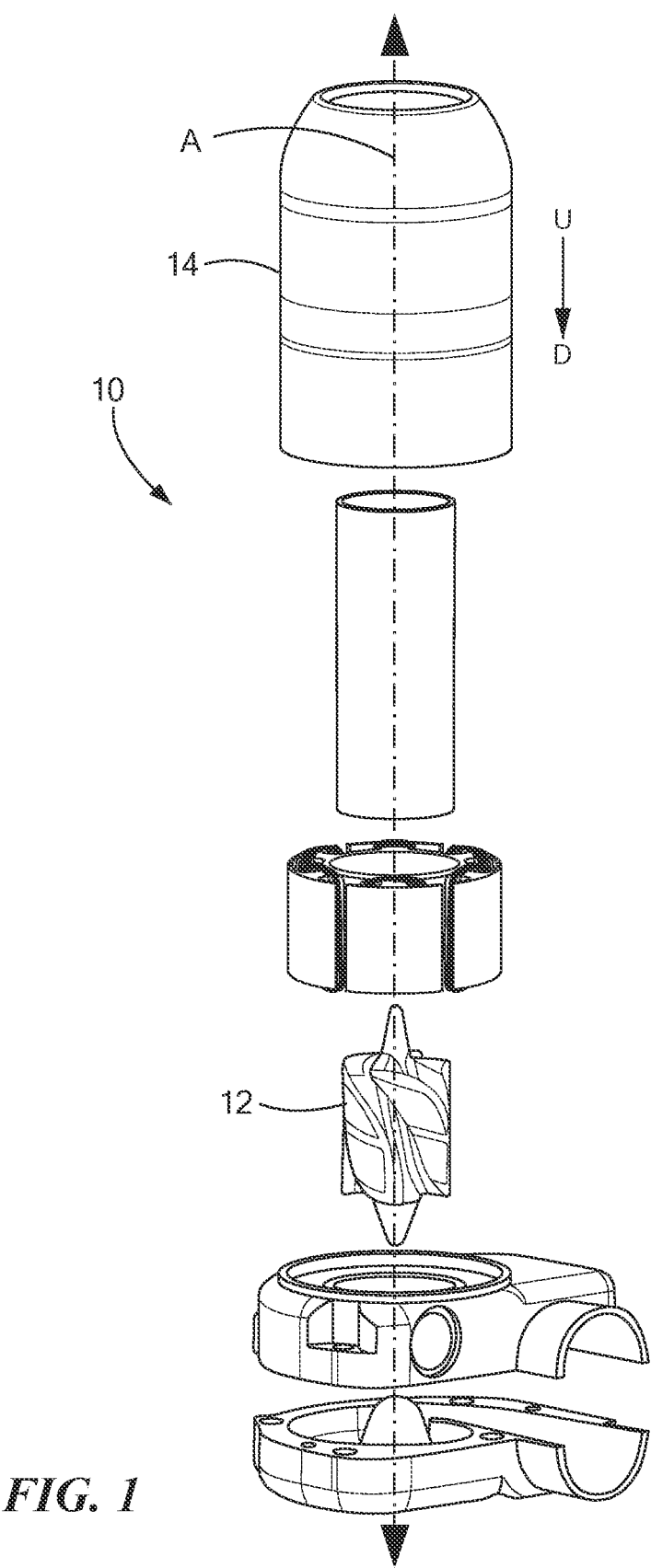
FIG. 1 is a disassembled view of an implantable blood pump.

Referring now to the drawings in which like reference designators refer to like elements there is shown in FIG. 1 a disassembled view of an exemplary implantable blood pump 10 configured to be implanted within a patient, such as a human or animal patient. The blood pump 10 may be, without limitation, the HVAD® Pump or the MVAD® Pump, having a movable element, such as an impeller 12 or a rotor, configured to rotate and impel blood from the heart to the rest of the body. The HVAD® Pump is further discussed in U.S. Pat. Nos. 7,997,854 and 8,512,013, the disclosures of which are incorporated herein by reference in the entirety. The MVAD® Pump is further discussed in U.S. Pat. Nos. 8,007,254, 8,419,609, and 9,561,313, the disclosures of which are incorporated herein by reference in the entirety.

Figure 2:
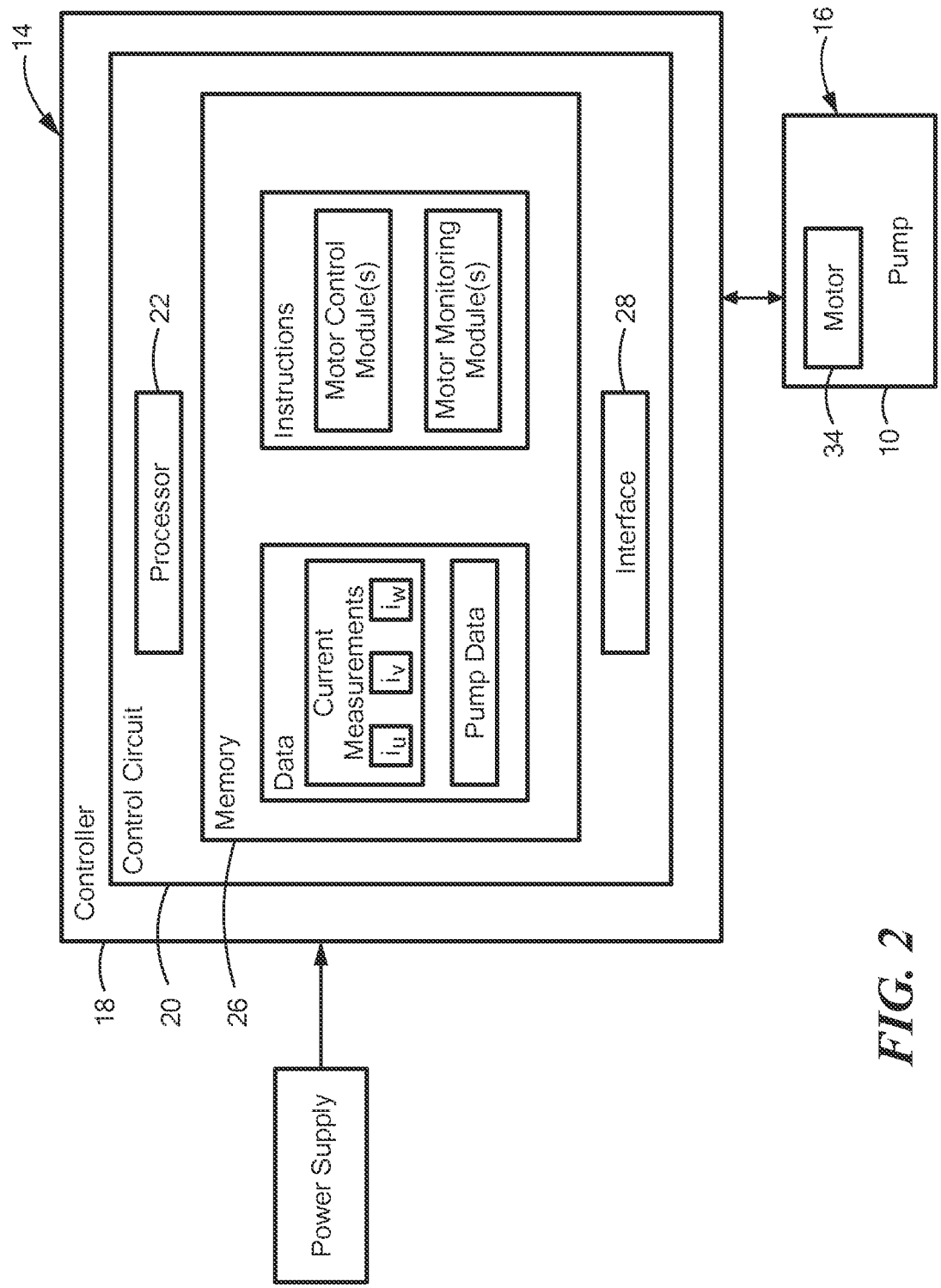
FIG. 2 is a block diagram of a system for controlling a pump speed of the blood pump of FIG. 1.

FIG. 2 is a block diagram of an exemplary system 14 for controlling a pump speed and/or other operations of the implantable blood pump 10 when the blood pump 10 is in communication with the system 14. The blood pump 10 includes a motor 16 therein and may be a separate component or form part of the system 14. In one example, the system 14 includes a controller 18 having a control circuit 20 and a processor 22 including processing circuitry 24 configured to perform the operations of the blood pump 10. The system 14 may also include a memory 26 and an interface 28, the memory 26 being configured to store information accessible by the processor 22, including instructions executable by the processing circuitry 24 and/or data that may be retrieved, manipulated or stored by the processor 22. Such instructions and/or data include that which is used to control the pump speed.

The processing circuitry 24 is configured to initiate a suction response algorithm when certain triggers are met. Such suction response algorithms may include, but are not limited to, reducing the speed of the impeller 12 of the pump 10 to various speeds depending on certain criteria. Such an algorithm may be found at least in U.S. patent application Ser. No. 16/795,929, the entirety of which is incorporated by reference herein. In particular, the processing circuitry 24 triggers a suction response algorithm when the following criteria is met:

$$x_1 S + x_2 N \geq 1$$

Where $(x_1)$ is a suction event variable or a suction cost, $(x_2)$ is a non-suction event variable or a non-suction cost, (S) is a number of one-second suction events, and (N) is a number of one-second non-suction events. In particular, during, for example, a thirty second window of time, suction events and non-suction events are binarized into one-second events such that at most thirty suction or non-suction events can occur during any thirty second window.

For example, if 5 consecutive one-second suction events occur and trigger the suction response algorithm then:

$$x_1 5 + x_2 0 = 1$$

$$x_1 = 0.2$$

If 6 suction events in 10 seconds also trigger then suction response algorithm then:

$$0.2*6 + x_2*4 = 1$$

$$x_2 = -0.05$$

And, if 8 suction events occur in 20 seconds also trigger then suction response algorithm then:

$$0.2*8 + x_2*12 = 1$$

$$x_2 = -0.05$$

Therefore, in one embodiment, the suction response algorithm is triggered if:

$$0.2*S - 0.05*N = 1$$

In another words, to avoid triggering the suction response algorithm, four non-suctions events are needed to account for one suction event, however, a higher concentration of suction events causes the response algorithm to be activated faster. The above function is exemplary and in other configurations $x_1$ and $x_2$ may vary depending on the desired sensitivity to triggering a suction response algorithm. For example, if the clinician is desirous of less sensitivity to suction by requiring 10 one-second suction events in 10 seconds, than $x_1$ would equal 0.1 making the suction response less sensitive. In one configuration, the trigger for a suction response algorithm is time bound so the response is triggered by time. For example, the trigger may be a moving thirty second window. Moreover, the sum of the suction event variable and the non-suction event variable must be greater than zero. For example, 30 non-suction events in a thirty second window would be equal to 0 and not −1.5 such that any subsequent thirty second window does not have to climb from a negative value.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A controller for an implantable blood pump, comprising:
   a memory; and
   processing circuitry in communication with the memory, the processing circuitry configured to:
      multiply a number of suction events, of one or more suction events that occurred within a predetermined time period, by a suction event cost to generate a first output;
      compare the first output to a predetermined threshold to determine whether a suction condition has occurred;
      determine, based on comparing the first output to the predetermined threshold, whether the suction condition has occurred; and
      responsive to determining that the suction condition has occurred, control, according to a speed response algorithm, a speed of an impeller of the implantable blood pump to resolve the suction condition.

2. The controller of claim 1, wherein to determine whether the suction event has occurred, the processing circuitry is further configured to:
   multiply a number of non-suction events, of one or more non-suction events that occurred within the predetermined time period, by a non-suction event cost to generate a second output;
   add the first output and the second output to generate a third output; and
   compare the third output to the predetermined threshold to determine whether the suction condition has occurred.

3. The controller of claim 1, wherein the predetermined threshold is at least one.

4. The controller of claim 1, wherein the suction event cost is less than one.

5. The controller of claim 1, wherein the predetermined threshold is at least 0.

6. The controller of claim 1, wherein the processing circuitry is configured to determine each suction event of the one or more suctions events over a one-second time period.

7. The controller of claim 1, wherein the predetermined time period is 30 seconds.

8. A method of operating an implantable blood pump, comprising:
   multiplying, by processing circuitry of a controller for the implantable blood pump, a number of suction events, of one or more suction events that occurred within a predetermined time period, by a suction event cost to generate a first output;
   comparing, by the processing circuitry, the first output to a predetermined threshold to determine whether a suction condition has occurred;
   determining, by the processing circuitry and based on comparing the first output to the predetermined threshold, whether the suction condition has occurred; and
   responsive to determining that the suction condition has occurred, controlling, by the processing circuitry and according to a speed response algorithm, a speed of an impeller of the implantable blood pump to resolve the suction condition.

9. The method of claim 8, wherein determining whether the suction condition has occurred comprises:
   multiplying, by the processing circuitry, a number of non-suction events, of one or more non-suction events that occurred within the predetermined time period, by a non-suction event cost to generate a second output;
   add the first output and the second output to generate a third output; and
   comparing, by the processing circuitry, the third output to the predetermined threshold to determine whether the suction condition has occurred.

10. The method of claim 8, wherein the predetermined threshold is at least one.

11. The method of claim 8, wherein the suction event cost is less than one.

12. The method of claim 8, wherein the predetermined time period is 30 seconds.

13. The method of claim 8, wherein determining the number of suction events comprises determining, by the processing circuitry, each suction event of the one or more suction events over a one-second time period.

14. A system comprising:
   an implantable blood pump;
   a power source for the implantable blood pump; and
   a controller for the implantable blood pump, comprising:
      a memory; and
      processing circuitry in communication with the memory, the processing circuitry configured to:
         multiply a number of suction events, of one or more suction events that occurred within a predetermined time period, by a suction event cost to generate a first output;
         compare the first output to a predetermined threshold to determine whether a suction condition has occurred;
         determine, based on comparing the first output to the predetermined threshold, whether the suction condition has occurred; and
         responsive to determining that the suction condition has occurred, control, according to a speed response algorithm, a speed of an impeller of the implantable blood pump to resolve the suction condition.

15. The system of claim 14, wherein to determine whether the suction event has occurred, the processing circuitry is further configured to:
   multiply a number of non-suction events, of one or more non-suction events that occurred within the predetermined time period, by a non-suction event cost to generate a second output;
   add the first output and the second output to generate a third output; and
   compare the third output to the predetermined threshold to determine whether the suction condition has occurred.

16. The system of claim 14, wherein the predetermined threshold is at least one.

17. The system of claim 14, wherein the suction event cost is less than one.

* * * * *